United States Patent [19]
Giordano et al.

[11] Patent Number: 5,994,120
[45] Date of Patent: Nov. 30, 1999

[54] METHOD OF BIOREMEDIATING AN ORGANIC HAZARDOUS SUBSTANCE

[75] Inventors: Sara J. Giordano, W. Middlesex; Robert-A. Ollar, Milford, both of Pa.

[73] Assignee: Infectech, Inc., Sharon, Pa.

[21] Appl. No.: 09/023,677

[22] Filed: Feb. 13, 1998

[51] Int. Cl.$^6$ ................ B09B 3/00; C02F 3/00; A62D 3/00
[52] U.S. Cl. ............ 435/262.5; 588/205; 588/206; 210/610; 210/611
[58] Field of Search ............ 435/253.3, 262.5; 588/205, 206; 210/601, 610, 611

[56] References Cited

U.S. PATENT DOCUMENTS

| 4,713,343 | 12/1987 | Wilson, Jr. et al. | |
|---|---|---|---|
| 4,853,334 | 8/1989 | Vandenbergh et al. | |
| 5,079,166 | 1/1992 | Winter et al. | |
| 5,153,119 | 10/1992 | Ollar | 435/34 |
| 5,316,918 | 5/1994 | Ollar | 435/34 |
| 5,472,877 | 12/1995 | Ollar | 435/288.1 |
| 5,512,479 | 4/1996 | Steffan | 435/262.5 |
| 5,569,592 | 10/1996 | Ollar | 435/32 |
| 5,637,501 | 6/1997 | Ollar et al. | 435/286.2 |
| 5,639,675 | 6/1997 | Felder et al. | 435/29 |
| 5,641,645 | 6/1997 | Felder et al. | 435/32 |
| 5,654,194 | 8/1997 | Felder et al. | 435/287.9 |
| 5,663,056 | 9/1997 | Ollar et al. | 435/29 |
| 5,668,010 | 9/1997 | Felder et al. | 435/287.9 |
| 5,677,169 | 10/1997 | Ollar et al. | 435/287.9 |

OTHER PUBLICATIONS

King et al. "Practical Environmental Bioremedation", Lewis Publishers, Boca Raton, FL pp. 49–50, 84, 1992.

*Primary Examiner*—Wayne Langel
*Assistant Examiner*—Maribel Medina
*Attorney, Agent, or Firm*—David V. Radack; Eckert Seamans Cherin & Mellott, LLC

[57] ABSTRACT

A method of bioremediating an organic hazardous substance present in an aqueous environment having contained therein a microorganism is provided which comprises introducing into the aqueous environment a water insoluble, substantially nontoxic organic material. Further associated methods of bioremediating contaminated water using a tank containing a water insoluble, substantially nontoxic organic material are also disclosed.

31 Claims, 1 Drawing Sheet

METHOD OF BIOREMEDIATING AN ORGANIC HAZARDOUS SUBSTANCE

BACKGROUND OF THE INVENTION

This invention relates to methods of bioremediating an organic hazardous substance.

Environmental cleanup of industrial sites and water supplies is often mandated by federal and state governments. These cleanups can be extremely expensive and time-consuming. Traditional methods of environmental cleanup have focused on the use of physical means of removing the contaminant, such as air-sparging plus soil vapor extraction, or pump-and-treat systems. Both technologies ultimately transfer the hazardous substance, in a concentrated form, to a filter for disposal at a hazardous substance facility.

In stark contrast to these traditional environmental cleanup methods stands the relatively new field of bioremediation. Bioremediation can be technically defined as the conversion of an organic hazardous substance into a form which is less toxic or nontoxic. Bioremediation efforts to date, however, have focussed on cometabolic degradation of the organic hazardous substance (such as, for example, trichloroethylene (TCE)) by using compounds such as toluene, phenol, methane, methanol, propane or butane. All of these, themselves, are hazardous substances and their addition to, for example, a contaminated aquifer, even if they are biodegradable, is neither encouraged nor permitted in some cases.

What is needed, therefore, is a method that is effective in bioremediating organic hazardous substances, but which avoids using toxic materials.

SUMMARY OF THE INVENTION

The invention has met or exceeded the above-mentioned needs as well as others. A method of bioremediating an organic hazardous substance present in an aqueous environment having contained therein a microorganism is provided which comprises introducing into the aqueous environment a water insoluble, substantially nontoxic organic material. In this way, the organic hazardous substance is bioremediated without the need to use toxic materials, such as toluene.

A further method of the invention incudes providing a tank including an amount of a water insoluble, substantially nontoxic organic material therein and then subsequently introducing therein contaminated water including (i) a microorganism and (ii) the organic hazardous substance to be bioremediated. If the contaminated water does not contain, naturally, a microorganism, the invention also provides that the microorganism can be introduced into the tank.

BRIEF DESCRIPTION OF THE DRAWINGS

A full understanding of the invention can be gained from the following detailed description of the invention when read in conjunction with the accompanying drawings in which.

DETAILED DESCRIPTION

Figure 1:
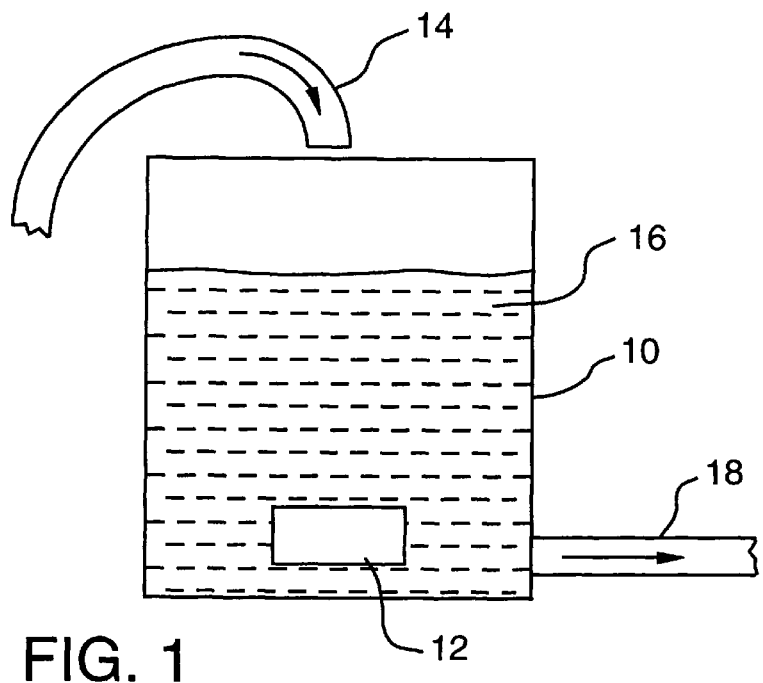
FIG. 1 is a schematic diagram of one embodiment of the invention.

As used herein, the term "organic hazardous substance" means any organic substance referred to in 42 U.S.C. § 9601(14) (which is expressly incorporated herein by reference) and any refined petroleum products. The term specifically includes natural and synthetic hydrocarbons. The hydrocarbons include halogenated hydrocarbons, such as chlorinated hydrocarbons, for example, trichloroethylene (TCE).

As used herein, the term "water insoluble, substantially nontoxic organic material" means any material on which a microorganism can attach, with the microorganism subsequently metabolizing the material and during metabolism producing an enzyme which cometabolizes an organic hazardous substance. The term includes, but is not limited to: liquid and solid paraffin; paraffin wax; and wax. The material is insoluble in water, is substantially nontoxic and is an organic material. By "substantially nontoxic" it is meant that the material does not cause damage to living tissue, impairment of the central nervous system, severe illness, or death when ingested, inhaled or absorbed by a living being.

As used herein, the term "microorganism" means a living organism of microscopic size including, but not limited to, bacteria, molds and fungi. A "paraffinophilic microorganism" is a microorganism that can employ paraffin as a source of carbon. A specific paraffinophilic microorganism can be a member of the genus Pseudomonas, such as *Pseudomonas putida*.

It has been found, quite surprisingly and unexpectedly, that introducing a water insoluble, substantially nontoxic organic material, such as paraffin, into an aqueous environment, such as an aquifer, that contains organic hazardous substances, such as trichloroethylene, will cause bioremediation of the aqueous environment. It is believed that microorganisms either naturally present in the aqueous environment or that are introduced therein from another source, attach to the material for use as a food source, produce an enzyme which cometabolizes the organic hazardous substance. The enzyme, which is an oxygenase, initiates organic hazardous substance contaminant degradation by breaking the bonds of the contaminant and incorporating molecular oxygen into the compound. The process ultimately results in the formation of innocuous substances such as carbon dioxide, water and metabolic intermediates. The mechanism by which the oxygenases associated with paraffin degradation mediate the organic hazardous substance, such as trichloroethylene (TCE), is unknown.

The water insoluble, substantially nontoxic material, as indicated above, can be liquid or solid paraffin; paraffin wax; or waxes. One method of the invention simply involves introducing into the aqueous environment an amount of the material. For example, a block of paraffin can be placed into the aquifer. This block of paraffin will most likely float, so this method would be effective to bioremediate organic hazardous substances that float near the top of the aquifer. The microorganism, in this aspect of the method, is already determined to be naturally present in the aquifer. The microorganism, such as *Pseudomonas aueroginosa*, will attach to the block of paraffin and utilize the paraffin as a food source. The metabolism of the paraffin by the microorganism will cause the production of an enzyme, such as an oxygenase, that will cometabolize the organic hazardous substance therein.

It will be appreciated that the material can also be coated on substrates, such as rods, plates, screens and beads, with the coated substrate then being placed into the aquifer. The coated substrate, if desired, can be anchored onto the floor of the aquifer. In another embodiment of the invention, a pipe with holes therein can be placed into the aquifer with the paraffin being placed into the pipe. Microorganisms can migrate through the holes onto the paraffin and the metabolism/cometabolism process, as described above, can take place.

If desired, conventional air sparging and/or nutrient supplementation can be utilized. This will increase the effectiveness of the bioremediation.

Another aspect of the invention will now be discussed with reference to the schematic diagram shown in FIG. 1. A tank 10 is provided which contains an amount of a water insoluble, substantially nontoxic organic material, such as a block of paraffin 12. Contaminated water 16, containing the hazardous substances to be bioremediated, is introduced into the tank 10 through pipe 14. The contaminated water 16 either contains, or has added to it, a microorganism. The contaminated water 16 is left standing in the tank 10 until the hazardous substances are bioremediated. The bioremediated water is then drained out of the tank 10 through pipe 18.

EXAMPLE

The following example will illustrate the effectiveness of the invention in bioremediating contaminated water containing TCE by using paraffin.

METHODS

Groundwater known to be contaminated with trichloroethylene (TCE) was collected at an industrial facility and immediately transported to a laboratory. The groundwater was analyzed and it was determined to contain a number of paraffinophilic microorganisms, such as *Pseudomonas putida, Pseudomonas fluorescens* and *Rhodococcus erythropolis*. The groundwater sample was filtered to remove particulate matter such as silt or sand. Reagent grade TCE was then added such that the final concentration of TCE in the groundwater sample was approximately twenty-five parts per million (25 ppm) as a weight/volume ratio (mg/l) to create the spiked groundwater. The spiked groundwater was thoroughly mixed and used to prepare three (3) test flasks corresponding to three different treatments:

TREATMENT A (Flask 1): Four parts of spiked groundwater were added to one part sterile, deionized water. This flask served as a control.

TREATMENT B (Flask 2): Four parts of spiked groundwater were added to one part sterile, nutrient supplement containing phenol as the sole carbon source.

TREATMENT C (Flask 3): Four parts of spiked groundwater were added to one part sterile, nutrient supplement containing paraffin as a sole carbon source.

All of the flasks were aerated by continuous magnetic stirring to ensure that oxygen would not be a limiting factor for microbial metabolism. Aliquots were removed from the flasks and sent to an independent laboratory (Environmental Sciences Corp. of Mt. Juliet, Tenn.) for quantitative analysis of TCE.

RESULTS AND DISCUSSIONS

Figure 2:
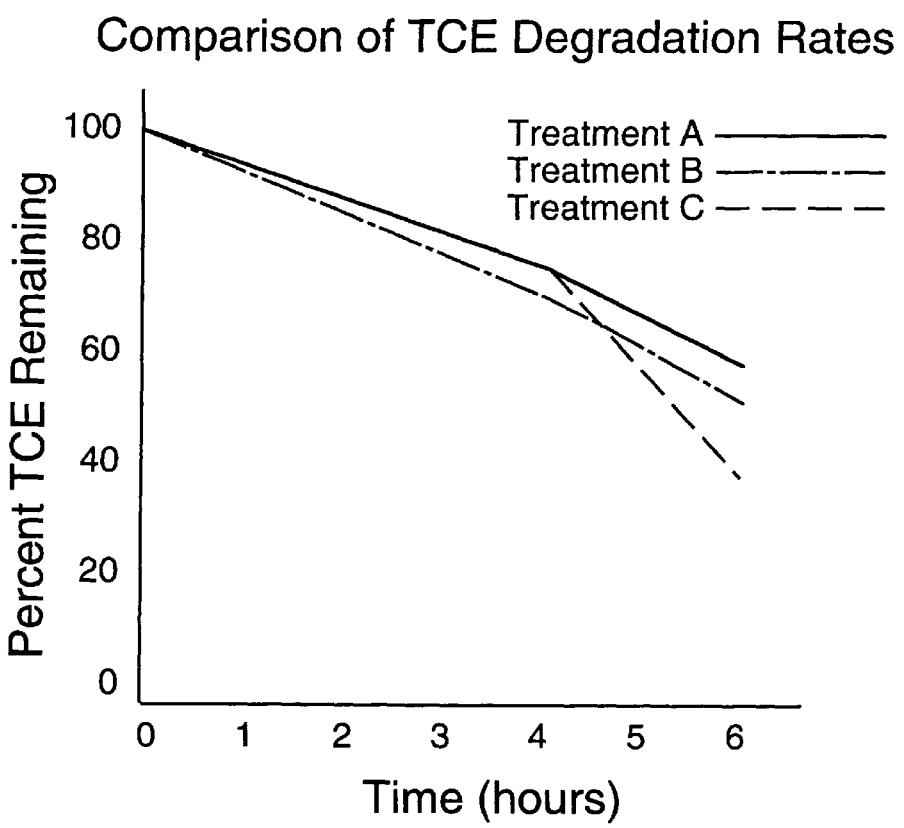
FIG. 2 is a graph showing a comparison of TCE degradation rates.

The analytical values were analyzed to determine the percent of TCE remaining as a function of time for each TREATMENT A, B and C. FIG. 2 shows those results.

As can be seen, after about 4 hours, the rate of degradation of the TCE in TREATMENT C (paraffin) was much increased over that of TREATMENT A (control) and TREATMENT B (phenol). Extrapolation of the curves associated with TREATMENT B and TREATMENT C indicates that complete degradation of TCE (none remaining) would occur within 11 and 8 hours, respectively. In other words, the time interval for the cometabolic degradation of TCE using paraffin is 37% less than that using phenol. Thus, the TREATMENT B using phenol, although faster than the control flask TREATMENT A, was not nearly as fast as TREATMENT C, using paraffin, in accordance with the invention. These surprising and unexpected results suggest that paraffin is superior to phenol in increasing the rate of TCE degradation. Other researchers have shown that usage of phenol, in contrast to methane, toluene and methanol, resulted in the highest rate of TCE cometabolic degradation. See, e.g., "An Evaluation Of Five Aerobic Cometabolic Substrates For Trichlorethylene Treatment By Microbes Stimulated From The Subsurface Of McClellan Air Force Base", *In Situ And On-Site Bioremediation: Volume* 3, pp. 93–99, Batelle Press (1997). Extrapolating those results with the results of this experiment, leads to the conclusion that using paraffin, a water insoluble, substantially nontoxic organic material, gives superior, unexpected and surprising results over prior art treatments utilizing the most common toxic substances used in bioremediation, i.e., phenol, methane, toluene and methanol, with the added benefits of using a nontoxic substance.

It will be appreciated that an effective and efficient method of bioremediating an aqueous environment containing organic hazardous substances has been provided. The method uses easily obtainable and inexpensive nontoxic materials such as paraffin and naturally occurring, safe microorganism such as those in the Pseudomonas genus.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of bioremediating an organic hazardous substance present in an aqueous environment having contained therein a paraffinophilic microorganism, said method comprising introducing into said aqueous environment a water insoluble, substantially nontoxic alkane of the formula $C_nH_{2n+2}$, wherein n is at least 18.

2. The method of claim 1, wherein
said water insoluble, substantially nontoxic alkane is a solid material.

3. The method of claim 1, wherein
said water insoluble, substantially nontoxic alkane is a liquid material.

4. The method of claim 1, wherein
said water insoluble, substantially nontoxic alkane is paraffin.

5. The method of claim 1, wherein
said organic hazardous substance is a halogenated hydrocarbon.

6. The method of claim 5, wherein
said halogenated hydrocarbon is a chlorinated hydrocarbon.

7. The method of claim 6, wherein
said chlorinated hydrocarbon is trichloroethylene.

8. The method of claim 1, wherein
said water insoluble, substantially nontoxic alkane is solid paraffin;
said paraffinophilic microorganism is selected from the group consisting of the Pseudomonas genus; and
said organic hazardous substance is trichloroethylene.

9. The method of claim 1, wherein
said water insoluble, substantially nontoxic alkane is a solid material coated on a substrate before being introduced into said aqueous environment.

10. The method of claim 9, wherein
said substrate is selected from the group consisting of a rod, beads, a plate and a screen.

11. The method of claim 9, wherein
said substrate includes means for anchoring said substrate in said aqueous environment.

12. The method of claim 1, including
seeding said aqueous environment with said paraffinophilic microorganism before introducing said water insoluble, substantially nontoxic alkane therein.

13. The method of claim 1, including
seeding said water insoluble, substantially nontoxic alkane with said paraffinophilic microorganism before introducing said water insoluble, substantially nontoxic alkane into said aqueous environment.

14. The method of claim 1, including
sparging an oxygen supplement into said aqueous environment.

15. The method of claim 1, including
introducing into said aqueous environment a nutrient supplement.

16. A method of bioremediating an organic hazardous substance contained in contaminated water, said contaminated water including a paraffinophilic microorganism therein, said method comprising:
providing a tank including an amount of a water insoluble, substantially nontoxic alkane of the formula $C_nH_{2n+2}$, wherein n is at least 18 contained therein; and
introducing into said tank said contaminated water.

17. The method of claim 16, wherein
said water insoluble, substantially nontoxic alkane is a solid material.

18. The method of claim 16, wherein
said water insoluble, substantially nontoxic alkane is a liquid material.

19. The method of claim 16, wherein
said water insoluble, substantially nontoxic alkane is paraffin.

20. The method of claim 16, wherein
said organic hazardous substance is a halogenated hydrocarbon.

21. The method of claim 20, wherein
said halogenated hydrocarbon is a chlorinated hydrocarbon.

22. The method of claim 21, wherein
said chlorinated hydrocarbon is trichloroethylene.

23. The method of claim 16, wherein
said water insoluble, substantially nontoxic alkane is solid paraffin;
said paraffinophilic microorganism is selected from the group consisting of the Pseudomonas genus; and
said organic hazardous substance is trichloroethylene.

24. A method of bioremediating an organic hazardous substance contained in contaminated water, said method comprising:
providing a tank including an amount of a water insoluble, substantially nontoxic alkane of the formula $C_nH_{2n+2}$, wherein n is at least 18 contained therein;
introducing into said tank said contaminated water containing said organic hazardous substance; and
introducing into said tank a paraffinophilic microorganism.

25. The method of claim 24, wherein
said water insoluble, substantially nontoxic alkane is a solid material.

26. The method of claim 24, wherein
said water insoluble, substantially nontoxic alkane is a liquid material.

27. The method of claim 24, wherein
said water insoluble, substantially nontoxic alkane is paraffin.

28. The method of claim 24, wherein
said organic hazardous substance is a halogenated hydrocarbon.

29. The method of claim 28, wherein
said halogenated hydrocarbon is a chlorinated hydrocarbon.

30. The method of claim 29, wherein
said chlorinated hydrocarbon is trichloroethylene.

31. The method of claim 24, wherein
said water insoluble, substantially nontoxic alkane is solid paraffin;
said paraffinophilic microorganism is selected from the Pseudomonas genus; and
said organic hazardous substance is trichloroethylene.

* * * * *